United States Patent [19]
Cusack et al.

[11] Patent Number: 5,134,079
[45] Date of Patent: Jul. 28, 1992

[54] FLUID SAMPLE COLLECTION AND DELIVERY SYSTEM AND METHODS PARTICULARLY ADAPTED FOR BODY FLUID SAMPLING

[75] Inventors: Robert F. Cusack; Michael D. Mintz, both of Edison, N.J.

[73] Assignee: International Technidyne Corp., Edison, N.J.

[21] Appl. No.: 329,340

[22] Filed: Mar. 27, 1989

[51] Int. Cl.⁵ .......................................... G01N 35/08
[52] U.S. Cl. ....................................... 436/53; 436/52; 422/81; 422/82
[58] Field of Search ....................... 422/81, 82; 436/52, 436/53

[56] References Cited

U.S. PATENT DOCUMENTS

| | | | |
|---|---|---|---|
| 2,797,149 | 6/1957 | Skeggs | 436/53 |
| 2,879,141 | 3/1959 | Skeggs | 73/864.24 |
| 2,935,028 | 5/1960 | Ferrari et al. | 417/475 |
| 3,134,263 | 5/1964 | De Jong | 73/864.25 |
| 3,167,397 | 1/1965 | Skeggs et al. | 422/82 |
| 3,230,776 | 1/1966 | Isreeli et al. | 73/864.25 |
| 3,241,432 | 3/1966 | Skeggs | 436/53 |
| 3,251,229 | 5/1966 | Isreeli et al. | 73/864.25 |
| 3,252,327 | 5/1966 | Ferrari | 73/864.25 |
| 3,266,322 | 8/1966 | Negersmith et al. | 73/864.22 |
| 3,282,651 | 11/1966 | Ferrari et al. | 422/82 |
| 3,524,366 | 8/1970 | Hrdina | 137/1 |
| 3,582,234 | 6/1971 | Isreeli et al. | 417/53 |
| 3,654,959 | 4/1972 | Kassel | 137/605 |
| 3,695,281 | 10/1972 | Leon | 137/1 |
| 3,826,615 | 7/1974 | Smythe et al. | 436/53 |
| 4,002,269 | 1/1977 | Negersmith et al. | 422/82 X |
| 4,028,056 | 6/1977 | Snyder et al. | 436/53 X |
| 4,127,111 | 11/1978 | Drolet | 422/81 X |
| 4,219,530 | 8/1980 | Kopp et al. | 422/81 X |
| 4,303,376 | 12/1981 | Siekmann | 604/249 X |
| 4,328,185 | 5/1982 | Reasons et al. | 422/81 X |
| 4,657,027 | 4/1987 | Paulsen | 436/52 X |
| 4,784,157 | 11/1988 | Halls et al. | 128/762 |
| 4,786,394 | 11/1988 | Enzer et al. | 436/52 X |

Primary Examiner—Robert J. Warden
Assistant Examiner—Stephanie Blythe
Attorney, Agent, or Firm—Arthur L. Plevy

[57] ABSTRACT

There is disclosed apparatus for transporting a sample of body fluid such as blood from a first location to a remote test site location. The apparatus operates in conjunction with a fluid manifold module which has a first sample input port, a second washing fluid input port and a third input port for receiving air. There are tubing means coupled to said first, second and third input ports which are coupled together and coupled to a sample output line which extends from the first location to the remote location. The manifold means contains check valves with one valve for blood and one valve for washing fluid and a diaphragm pump for air. There are logic means which selectively operate the valves and pump to allow the sample line to receive a sample separated by air barriers from washing fluid solution. In this manner, a predetermined volume of sample is transported from the first location to the remote test site location. At the test site location, the presence of sample is detected by detection means and the sample is directed to a test site. The remainder of materials such as the washing fluid and air are discharged at the remote location. The system includes flexible tubing and the fluids as present are pumped from the first locaiton to the remote location by means of a peristaltic pump or other pump in direct contact with the tubing.

34 Claims, 7 Drawing Sheets

FLUID SAMPLE COLLECTION AND DELIVERY SYSTEM AND METHODS PARTICULARLY ADAPTED FOR BODY FLUID SAMPLING

BACKGROUND OF THE INVENTION

This invention relates to a therapy control system for body fluid sampling and more particularly to blood sampling apparatus and methods which operate to collect a sample of blood, to transport that sample of blood to a location remote from the site of sample collection and thereafter to dispense the blood sample such that in vitro diagnostic blood tests may be performed.

Modern medical procedures require numerous tests to be performed on blood samples in regard to clotting characteristics, blood gas concentrations, blood chemistries and various other tests. These tests are required for a patient under treatment in a hospital or other facility. In typical techniques blood is usually manually drawn from the patient's vein, artery or from tubing through which the patient's blood is circulated external to the body. The amount of blood drawn and the frequency of collection from a patient is a function of the number of tests that have to be performed. In any event, a relatively large number of blood samples are frequently required at great inconvenience to the medical staff and discomfort to the patient.

The monitoring of a hospital patient's condition, particularly those confined to intensive care or undergoing various surgical or vascular-invasive procedures, is often accomplished by means of testing blood samples collected at regular time intervals. These means usually require the use of a needle for collection of from 3 to 10 ml. of blood per test. Traditional methods of collecting and testing such blood samples are wasteful, cumbersome and time consuming. Thus, it is usual for such sampling to be limited by practical considerations to intervals of 6 to 24 hours in the clinical situation and, with considerably greater difficulty, to intervals as short as every 15 to 30 minutes in surgical and vascular-invasive procedures. The resultant data frequently misses rapidly changing physiological conditions that are of clinical significance.

It is, therefore, an object of the present invention to provide a system whereby one can repeatedly collect and transport discrete blood samples by means of various conduits or tubes to a test site or suitable container. As will be explained, the apparatus operates to direct samples of blood taken directly from a patient or in vivo reservoir. In this manner the apparatus operates to direct the blood samples to a test site or suitable container that can be remotely located from the physical location of the patient and where various tests can be performed on the samples.

It is a further object of the present invention to assure that the entire tubing and system components are automatically cleaned and flushed prior to introduction into the system of the body fluid to be tested. In this manner the entire procedure automatically transports the blood to a test site and does so without the fear of contamination of the blood samples or contamination of the patient by the apparatus or by the methods of controlling the apparatus.

It is yet a further object of the present invention to provide control of the size of the blood sample so as to meet the requirements of the test apparatus adapted to this invention and limit the waste of patient blood.

It is still a further object of the present invention to draw a sample of blood from an in vivo patient source and thereafter to maintain in an open or unclogged condition the route through which that sample is drawn.

PRIOR ART

It is well known to transport body fluids to be diagnostically analyzed through tubular conduits. Many such systems separate discrete samples of the fluid by means of bubbles of an immiscible fluid which, for example, may be a gas as air and so on. J. Isreeli in U.S. Pat. Nos. 3,230,776 and 3,251,229 teaches that distinct blood samples may be aspirated from containers, separated by air bubbles and transported serially to an analyzer system. It is further noted that the action of the bubbles serves to aid in cleansing of the tubular walls to thereby limit cross contamination between successive fluid samples. In U.S. Pat. No. 3,241,432, Skeggs further teaches that alternate fluid segments within the tube may comprise a washing solution, further to cleanse said walls between the fluid samples to be analyzed. This same principle is acknowledged in many other patents, including: K. Negersmith et al 3,266,322; and A. Ferrari 3,252,327, which patents, in addition, demonstrate a tubular take-off probe through which air bubbles are aspirated following alternating immersions of the probe tip into open containers of sample fluids and washing liquids. It is also well known to inject air into the tubular fluid stream to create fluid segmentation by an immiscible bubble as demonstrated in Kassel U.S. Pat. No. 3,654,959, Apr. 11, 1972; Hrdina, U.S. Pat. No. 3,524,366, Aug. 18, 1970; and W. J. Smythe, U.S. Pat. No. 3,826,615, Jul. 30, 1974. U.S. Pat. No. 3,695,281 issued Oct. 3, 1972 to L. P. Leon demonstrates that the injected air bubble size may be controlled. A. Ferrari Jr. et al, 2,935,028 shows that proportioning fluid pumping rates may be achieved by simultaneous peristaltic pumping action on parallel elastomeric tubes of differing internal diameters. J. Isreeli, 3,582,234, Jun. 1, 1971 teaches close tolerance adjustment of the flow rate of fluids controlled by a peristaltic pump by stretching the tubing to vary the internal diameter accordingly.

SUMMARY OF THE INVENTION

Apparatus for transporting a sample of body fluid such as blood from a first location to a test site location, comprising sample tubing means having at a first end a sample input port, a second washing fluid such as saline input port and a third input port for receiving a fluid which is relatively immiscible with said sample, such as air, and said washing fluid and having at a second end an output port, and having second washing fluid tubing means coupled to said second washing fluid input port, a first pumping means coupled to said sample tubing means operative to direct the flow of fluids to said output port, second pumping means coupled to said second washing fluid tubing means operative to direct the flow of washing fluid through said second washing fluid input port into said sample tubing means and co-operative with said first pumping means to control the ratio of fluid volumes pumped by said first pumping means and said second pumping means in a first mode of operation to thereby cause washing fluid to flow within said sample tubing means from said washing fluid input port towards both said sample input port and said output port, first valving means coupled to said sample tubing means operative when selected in a second mode of operation to impede the flow of fluids to said output port thereby to divert all the flow of washing fluid from said washing fluid inlet port to said sample inlet port, second valving means coupled to said second washing fluid tubing means operative when selected in a third mode of operation to impede the flow of washing fluid through said second washing fluid input port into said sample tubing means, third metered pumping means coupled to said third input port for injecting a controlled volume of said immiscible fluid through said third input port when selected in said first and third modes of operation to thereby produce in said sample tubing means a series of discrete immiscible fluid bubbles dispersed within said body fluid or said washing fluid, control means coupled to said pumping means and said valving means for selectively energizing said pumping and said valving means in predetermined sequences to cause said output port to receive a given sequence of fluids as a series of cells of washing fluid separated by bubbles of said immiscible fluid in said first mode of operation or as a series of cells of body fluid separated by bubbles of said immiscible fluid following said third mode of operation, said output port directed to a remote location including said test site, said sample tubing means having detecting means at said remote location for monitoring said sequence of fluids and for providing output signal levels indicative of samples, washing fluid and immiscible fluid at said remote location and, means coupled to said sample tubing means and responsive to said output signal levels for moving said second end of said sample tubing to said test site location when said output signal is indicative of the presence of sample as contained in said series of cells of body fluids whereby only the contents of one selected cell of body fluid is directed to said test site location when said second end is moved and for discarding said body fluid, washing fluid and immiscible fluid in response to said signal levels when the selected cell of body fluid is not detected.

DETAILED DESCRIPTION OF THE FIGURES

Figure 1:
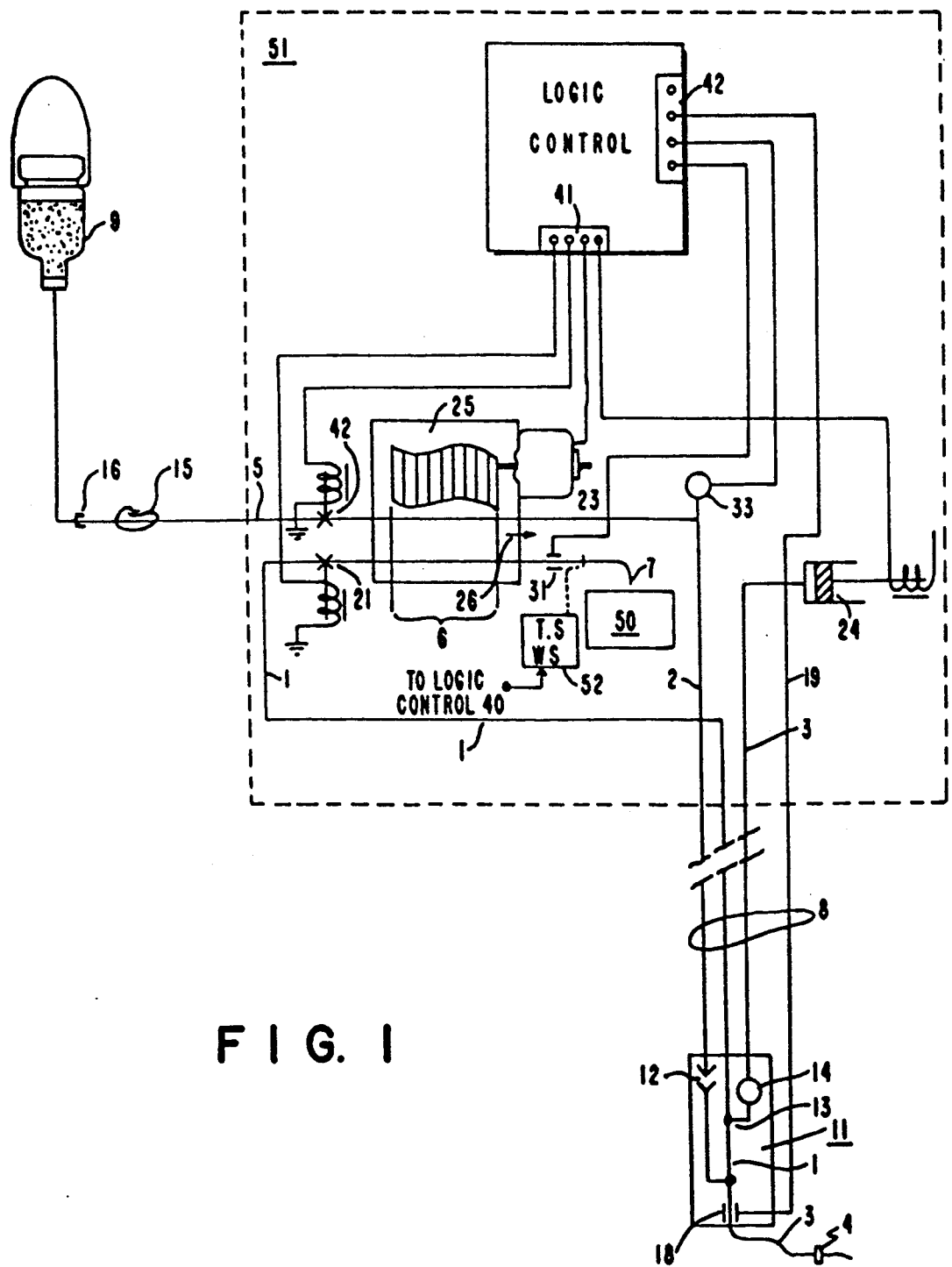
FIG. 1, is a block diagram depicting a repetitive discrete sample body fluid sampling apparatus according to this invention.

Referring to FIG. 1, there is shown a block diagram of a repetitive discrete blood sampling apparatus according to this invention. It is of course understood that while the system depicted can deliver blood samples to a test site or suitable container any body fluid can be accommodated as well and hence the system can be referred to as a fluid sample collection and delivery system. As seen in FIG. 1, there is shown a blood sample supply line or flexible sample transfer tube 1, terminated at an inlet end with a catheter 4. The catheter 4 may be inserted directly into a patient's blood vessel or an extracorporeal source of fluid to be analyzed. An outlet end of transfer tube 1 is coupled to a sample delivery nozzle 7 that is associated with a blood sample analyzer 50. Blood sample analyzers 50 are widely available and such equipment operates to analyze or perform tests on dispensed blood samples. Shown coupled to the nozzle 7 and the tube is a module 52 designated as TS/WS/SS. This module 52 may be a solenoid or other device which pushes tube 1 and nozzle 7 from a test site (TS) location to a waste site (WS) location or a sample site (SS) location. As will be explained, the system via the detector 31 determines when a true blood sample is at the nozzle 7 and dispenses the sample at the test site to the analyzer 50 or a suitable sample container at a sample delivery site. In all other modes the nozzle 7 releases the fluids into a waste receptacle at a waste site or a suitable sample container. When a true blood sample is at nozzle 7 logic control 40 operates the TS/WS/SS module 52 to position the nozzle at the test site from the waste or sample site. As one can ascertain many devices can operate to do so. The blood sample transfer tube 1 may consist of a plastic tube of approximately 0.085 inches outer diameter and having an inner diameter of 0.040 inches by way of example.

A washing fluid solution inlet port 12 is coupled to transfer tube 1 at a point as close to the catheter 4 as practical, as four to six inches for example. The term "washing fluid" includes isotonic solutions such as an injectable normal saline. A second inlet port 13 is coupled to transfer tube 1 approximately one inch from washing fluid solution inlet port 12 on the side opposite the inlet end. The inlet port 13 is employed for introduction of a fluid which is relatively immiscible with the blood sample and washing fluid solution. The impellers of a peristaltic pump 25 co-act with transfer tube 1 over a section 6 near sample delivery nozzle 7 to create a peristaltic action for drawing fluid through transfer tubing 1 and out to nozzle 7. Peristaltic pumps which operate to direct or pump fluid within a flexible tube are well known and many examples of such pumps exist in the prior art. While a single pump is shown to drive the washing fluid and sample lines it is understood that first and second pumps can be employed as well. If separate pumps are employed the control of the flow rate is simplified. However one can configure the impellers or fingers of a simple pump 25 to obtain isolation between the washing fluid and sample lines as driven by a single pump. For purposes of minimizing sequential blood sample cross contamination, transfer tube 1 comprises as nearly as possible a single uninterrupted length of extruded elastomeric tubing, as silicone plastic for example, the surfaces of which are essentially hydrophobic and otherwise nonadherent to blood or liquid-blood-born medications or transformed blood components. Inlet ports 12 and 13 and catheter 4 attachment to transfer tube 1 are so constructed as to minimize the production of areas of fluid stagnation that might transfer residues between blood samples, as will be explained.

A washing fluid solution delivery tube 2 is coupled to inlet port 12 by way of one-way valve 17 for transporting washing fluid from the washing fluid reservoir 9. The impellers or fingers of peristaltic pump 25 co-act with the washing fluid delivery tube 2 over the same corresponding section 6 as with the sample tube to cause injection of washing fluid through washing fluid inlet port 12 into transfer tube 1. One-way valve/1, prevents periodic partial reversal of flow in washing fluid delivery tube 2 caused by the normal action of peristaltic pump 25. This assures that blood in sample transfer tube 1 can never be drawn through washing fluid inlet port 12. In order to assure that a greater volume of fluid may be caused to flow in washing fluid delivery tube 2 than in blood sample transfer tube 1 sections of tubes 1 and 2 as directed along area 6 are comprised of relatively identical elastomeric tubings. A constant ratiometric flow between these two tubes is achieved by the slight stretching of transfer tubing 1, relative to washing fluid solution delivery tube 2, as for example 10 percent. This stretch occurs in area 6 where one tube is stretched with respect to the other to control the flow volume. The sections 6 of tubes 1 and 2 are located in a cassette (FIG. 3) assembly which is associated with the pump and an instrument housing as will be explained. Thus, washing fluid may at times be injected into transfer tube 1 by way of inlet port 12 at a rate proportionally greater than the rate at which the peristaltic pump 25 draws fluid through transfer tube 1. A diaphragm-type pressure switch 33 connected to washing fluid delivery tube 2 serves to detect over-pressure conditions in both sample transfer tube 1 and washing fluid delivery tube 2 indicative of occlusion of catheter 4 or of the vessel from which blood samples are being collected.

The outlet of a fixed volume diaphragm pump 14 is directly connected to inlet port 13 of transfer tube 1 for injecting controlled volume bubbles of an immiscible fluid, such as air, into transfer tubing 1. The inlet to diaphragm pump 14, not shown, may be opened directly to ambient air or ducted by tubing means to a reservoir of the immiscible fluid material such as a nonvolatile fluorocarbon liquid. A solenoid driven pneumatic pump 24 driven by a control signal from logic controller 40 sends a pressure pulse through the tube 3. This pulse drives the diaphragm pump 14 resulting in the injection of a controlled volume bubble of immiscible fluid into sample transfer tube 1 by way of inlet port 13.

Figure 3:
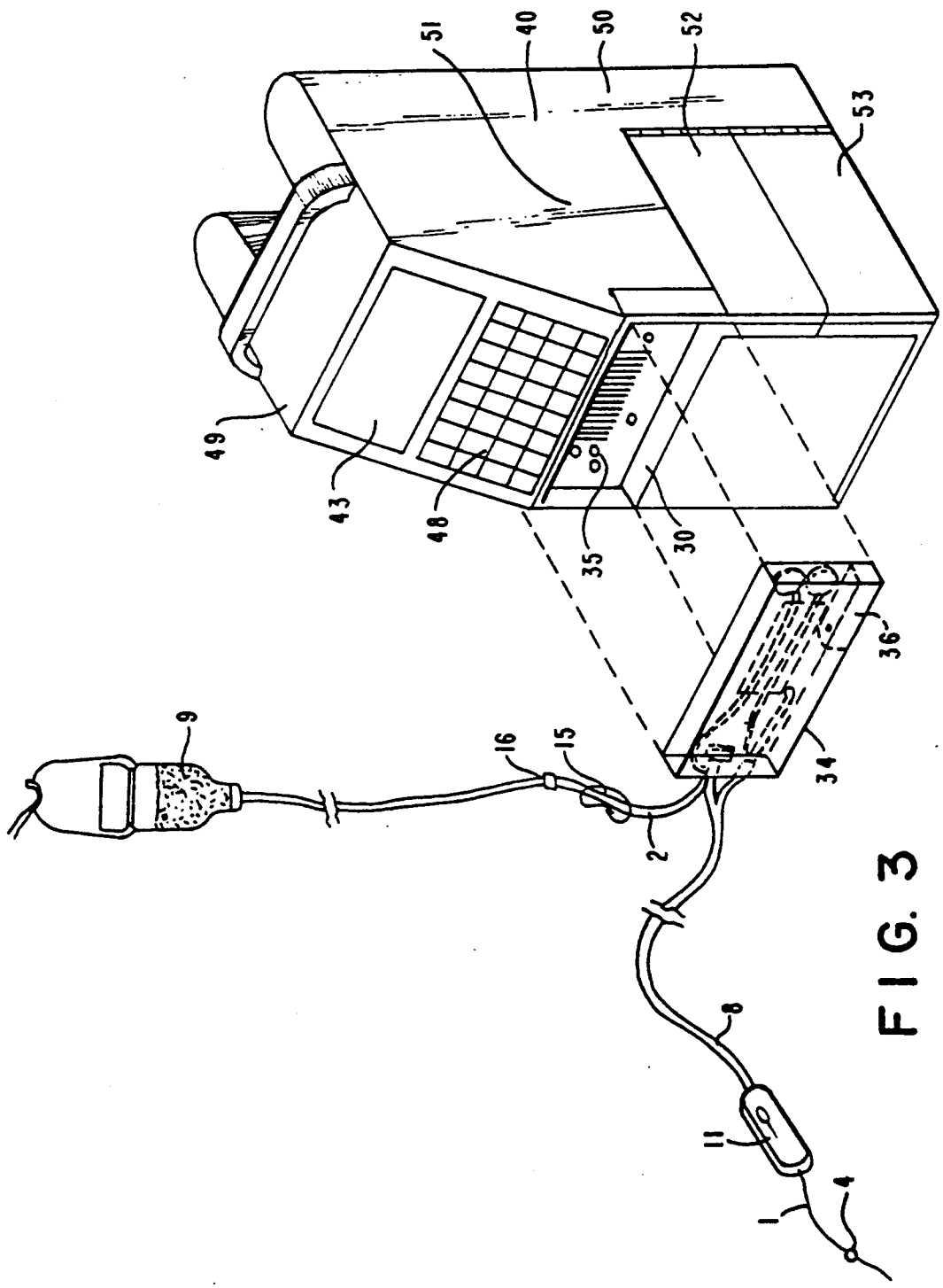
FIG. 3 depicts a practical system for blood sample collection, remote site delivery and diagnostic analysis.

Shown associated with the transfer tube 1 is a first tubing pinch valve 21 located at the inlet to the peristaltic pump. The valve 21 when activated, prevents the flow of fluids within transfer tube 1 between inlet port 13 and delivery nozzle 7. A second tubing pinch valve 22 is also located at the inlet to peristaltic pump and associated with washing fluid delivery tube 2. Valve 22, when actuated, prevents flow of washing fluid into transfer tube 1 by way of washing fluid inlet port 12. Pinch valves 21 and 22 are controlled by the logic controller 40 to permit independent fluid flow at various times in sample transfer tube 1 and washing fluid tube 2. As will be explained, valves 21 and 22 are located in the area adjacent to the cassette associated with the pump (FIG. 3). Peristaltic pumps in general provide a pulsed fluid flow. This operation is employed to great advantage in the scrubbing node as due to the pulse flow turbulences as achieved which enhances the scrubbing action. In the keep open flow mode, relatively constant flow is achieved by compensating for the known pinch off period of the pump and causing an increase in pump speed to maintain a more constant flow. This operation is achieved by monitoring the position of the rotational position of the pump so that the fluid pinch off zone is defined and using this information to optimize fluid delivery.

A fluid detector 18 is associated with blood sample transfer tube 1 and located at a point between the catheter 4 and washing fluid inlet port 12. The detector 18 identifies what fluid is passing within sample transfer tube 1 and otherwise serves as a bubble detector. A second fluid detector 31 associated with sample transfer tube 1 is located as close as practical to outlet nozzle 7, one to two inches for example, to identify what fluid is about to be dispensed.

Leads of the logic controller 40 are coupled through an output terminal board 41 to drive motor 23 of the dual channel peristaltic pump 25, pneumatic pump 24, tubing pinch valves 21 and 22. By way of signal input terminal board 41 controller 40 is connected to and is responsive to fluid or bubble detectors 18 and 31, and pressure switch 33 for coordinating the flow of the blood sample, washing fluid, and immiscible fluid within sample transfer tube 1 thereby to transport the blood sample from the inlet or catheter end to outlet or nozzle end.

Logic controller 40 is also adaptable to interface with various data input and output devices as shown in FIG. 3. These may include a display device 43, a keyboard 48, a printer (not shown), a standard data interface such as RS232 and connections to blood testing devices and infusion apparatus.

Logic controller 40 can be connected to all essential system functions so as to provide the desirable monitoring of said functions ensuring a high level of performance and safety. Further, logic controller 40 has the capability to store monitored data in memory and recall, in predetermined formats, pertinent data such as volume of blood drawn volume of fluids infused, and number of samples taken.

All system functions are monitorable and controllable through logic control 40 and the system is designed to provide maximum safety, comfort, performance, accuracy, and ease of use to the patient and clinician.

Control 40 can make certain decisions consistent with therapeutic practice in response to signals received from fluid sampler, test device and infusion apparatus.

It will be understood that from a practical perspective it is convenient to organize the various system components described into functional assemblies that place a minimum of hardware and attending patient discomfort at the site of sample fluid collection. Thus, inlet ports 12 and 13, diaphragm pump 14 one-way valve 17 and fluid detector 18 are all included within an assembly module 11. Module 11 of small dimensions as one inch wide, two inches long and 0.5 inches thick for example. Such an assembly may be conveniently taped to a patient's arm in close proximity to the insertion site of catheter 4. Module 11 is connected by way of a flexible umbilical 8 of three to eight foot length for example comprising sample transfer tube 1, washing fluid delivery tube 2, pneumatic tube 3 and fluid detector control and output lines 19 to instrument 51 (dashed lines) comprising the logic control 40, analyzer 50, pumps, valves, actuators and detectors. A tubing connector 16 and manual tubing pinch clamp 15 in washing fluid delivery tube 2 are provided for convenience in changing washing fluid reservoir 9 during instrument operation. The module 11 is shown in detail in FIGS. 4 and 5 and is referred to as a fluid manifold and bubble detector assembly.

For clarity in understanding the process of blood sample collection and system purging FIGS. 2A through 2K depict schematic detail of the contents and states of sample transfer tube 1 at various phases of operation. Identical structural features in these schematic drawings employ the same numerical designations as utilized in FIG. 1.

Figure 2A:
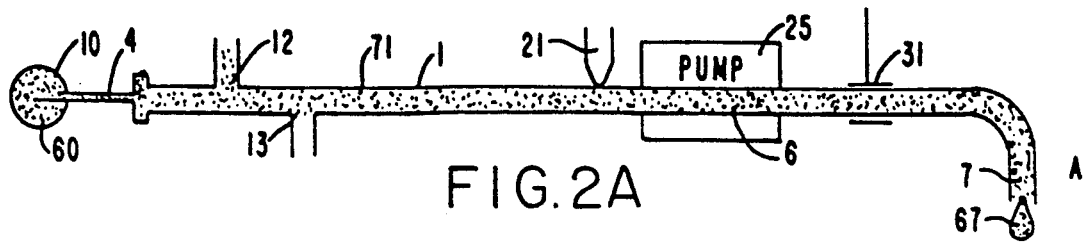
FIGS. 2A-2K depict schematic diagrams showing the exact steps implemented by the apparatus in order to transport a sample of blood from a patient site to a test site.

In FIG. 2A there is shown the sample transfer tube 1 filled with washing fluid solution except in the immediate region of catheter 4. In this phase of operation peristaltic pump 25 acting on the sample tubing 1 along section 6 has commenced drawing blood 60 from vessel 10, through catheter 4 and into the inlet end of sample transfer tube 1. No fluids are transferred in or out of sample transfer tube 1 at inlet ports 12 and 13. Droplet 67 of washing fluid displaced by the pumping action is dispensed from nozzle 7.

Figure 2B:
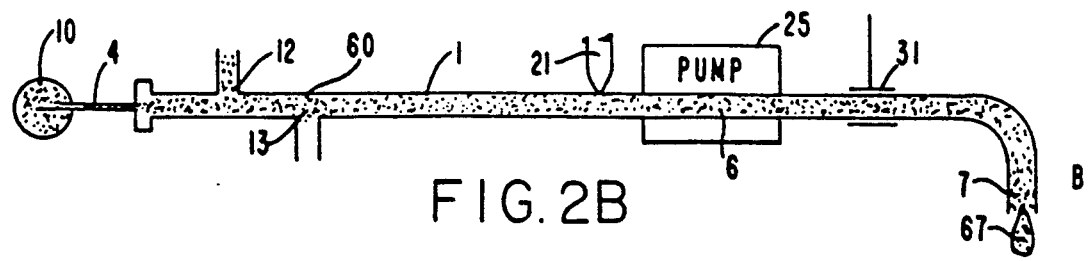

In FIG. 2B there is shown sample transfer tube 1 at a slightly later time as 0.25 seconds for example. Blood 60 has been drawn past inlet ports 12 and 13. It will be noted that some diffusion may cause blood to enter washing fluid inlet port 12, however the static condition of washing fluid in washing fluid delivery tube 2 otherwise inhibits significant penetration of blood into inlet port 12.

Figure 2C:
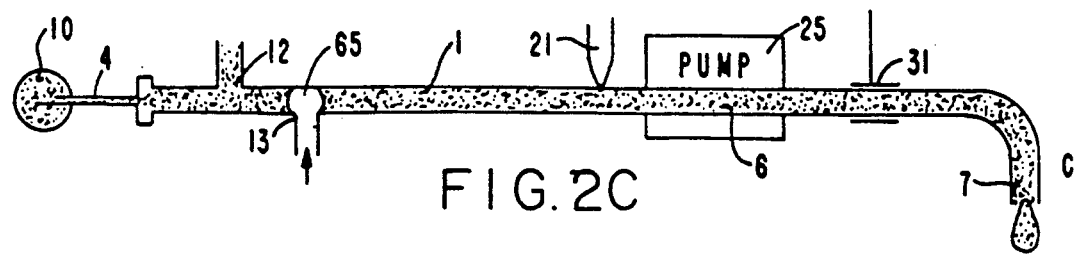

In FIG. 2C the condition in FIG. 2B is altered by the injection through inlet 13 of a small volume of immiscible fluid as seven to ten microliters of air. This forms a bubble 65 in the tube 1 of said immiscible fluid. The bubble 65 fills an entire cross section of sample transfer tube 1 but is of lineal extent not to exceed the linear distance between inlet port 13 and washing fluid inlet port 12. The bubble 65 creates an isolating barrier within the blood 60 that has been drawn into sample transfer tube 1. By restricting the lineal extent of bubble 65, it will be seen that reverse flow in sample transfer tube 1 as later described cannot cause infusion of any portion of bubble 65 into vessel 10.

Figure 2D:
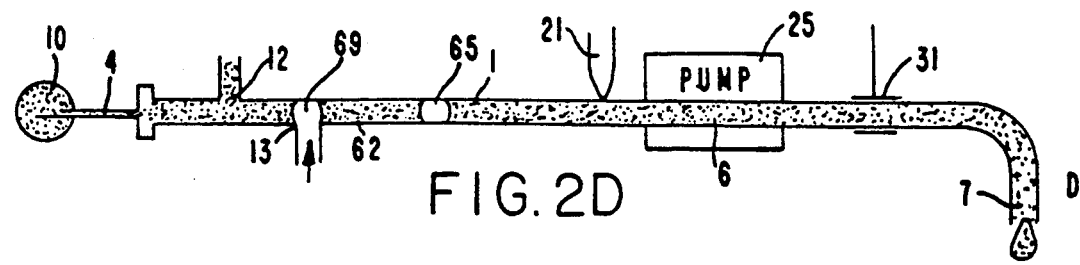
Figure 2E:
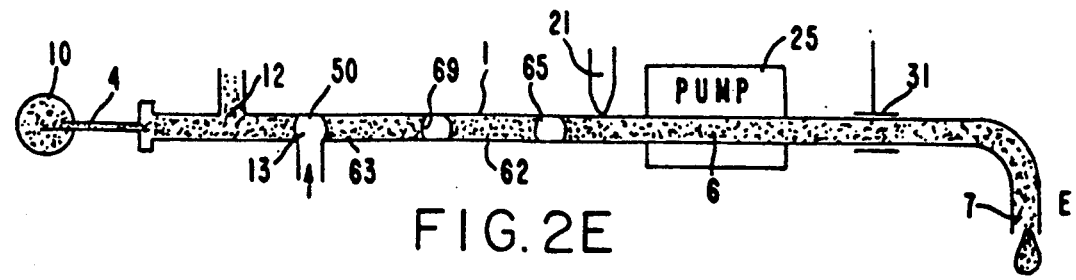

FIGS. 2D and 2E depict the same system at relatively later times when a second bubble 69 and third bubble 70 are caused to enter sample transfer tube 1 thereby creating isolated blood columns 62 and 63 each of 10 to 100 microliters for example. In function it is the purpose of leading blood column 62 to collect any residue of washing fluid that may remain in contact with the inner surfaces of sample transfer tube after passage of bubble 69. The bubble 69 further assures that any additional residuals on the inner surface of sample transfer tube 1 after passage of blood column 62 are indicative only of the characteristics of blood 60 alone as contained in isolated blood column 63. It will be understood that the number and lineal extent of isolated blood columns as 62 may be selected to best achieve the conditioning of the inner surfaces of sample transfer tube 1 prior to passage of the isolated blood column 63 that is to be analyzed.

Figure 2F:
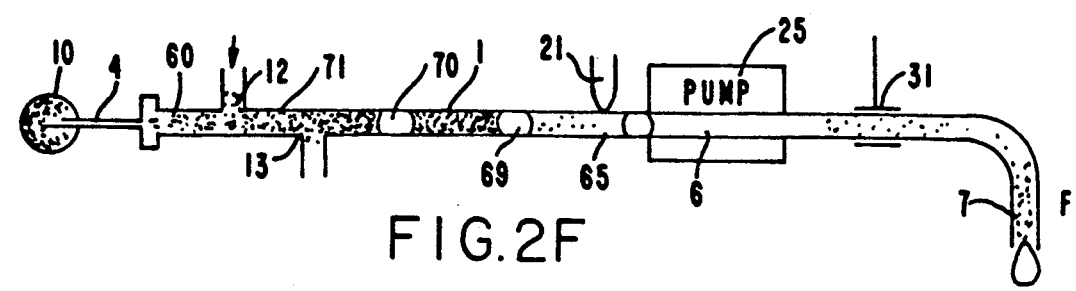

FIG. 2F depicts the same system approximately 0.1 seconds later. Washing fluid solution 71 has begun to enter sample transfer tube 1 by way of inlet port 12 at a rate slightly greater than the rate at which fluid is drawn by peristaltic pump 25 through sample transfer tube 1. Thus, blood 60 is caused to reverse its flow in sample transfer tube 1 at the entry point of washing fluid inlet port 12 and is reinfused into vessel 10 by way of catheter 4. It is the intent of such reverse flow to clear and maintain the sample transfer tube 1 clear of all traces of blood 60 between washing fluid inlet port 12 and catheter 4 and catheter 4 itself as nearly as possible.

Figure 2G:
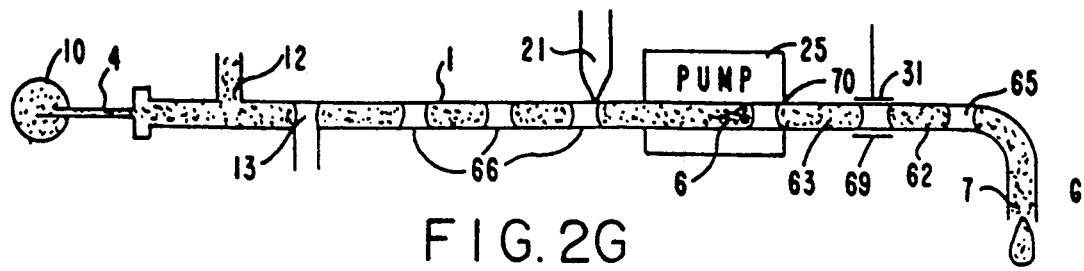

In FIG. 2G blood columns 62 and 63 have been directed further along sample transfer tube 1 to the point where the second bubble 69 has been detected by bubble detector 31 thereby identifying the location of the leading boundary of blood sample column 63. A train of bubbles 66 of immiscible fluid has been injected into the washing fluid contained in sample transfer tube 1 between immiscible fluid inlet port 13 and blood column 63. The train of bubbles 66 is employed to provide a scrubbing action on the inner surfaces of sample transfer tube 1 from inlet port 13 to thereby remove blood 60 residue that may affect subsequent blood samples. The reverse flow of washing fluid between catheter 4 and washing fluid inlet port 12 has caused all of the blood 60 previously contained in this tubing section to be reinfused into vessel 10. Thereafter, the continued reverse flow causes washing fluid to be infused through catheter 4 into vessel 10, both cleansing the inner surfaces of the tubing and catheter 4 and maintaining a "keep open flow."

Figure 2H:
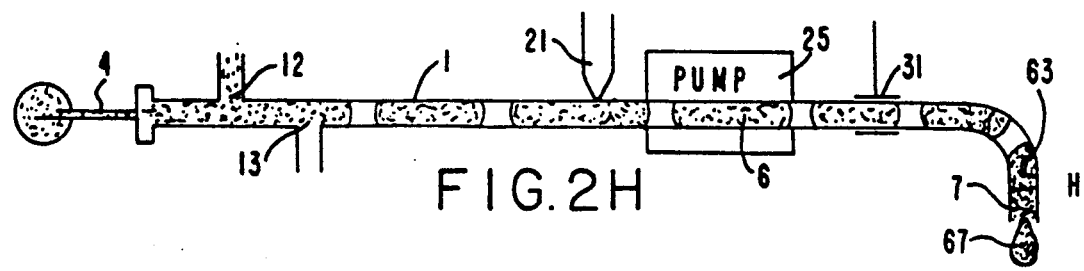

In FIG. 2H fluid has been further moved in sample transfer tube 1 to the point where the leading boundary of blood sample column 63 has been advanced to the open end of nozzle 7 and is ready for dispensing to blood testing device 50. Previously, fluid droplets as 67 in FIGS. 2A through 2H have been dispensed to a waste reservoir, not shown. When blood sample 63 is detected, the flexible tube end and nozzle 7 are moved by means of a solenoid or other device by the logic control 40 to direct nozzle 70 at the test site. Thus the positioning of the blood sample column is implemented by the logic control module 40 (FIG. 1). This is implemented by considering the given pre-set distance between detector 31 and the open end of nozzle 7 and known peristaltic pump 25 characteristics.

Figure 2I:
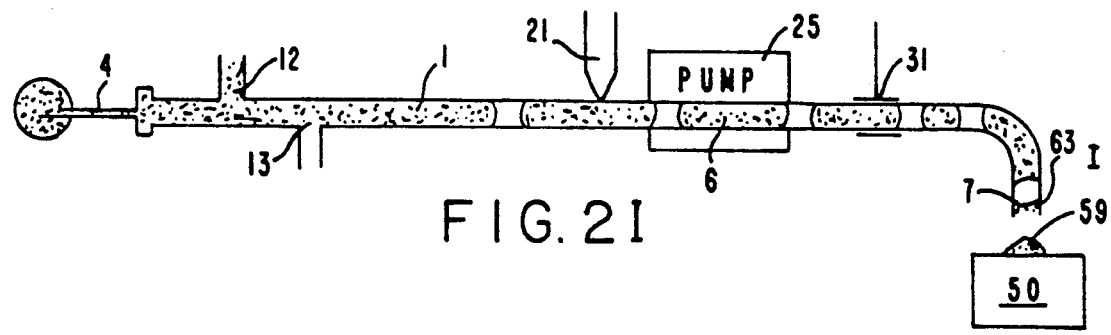

In FIG. 2I a measured portion 59 of blood sample column 63 is dispensed to the blood testing device 50 located at the test site as determined by control of peristaltic pump 25 by logic control module 40 in FIG. 1. The entire process as depicted in FIGS. 2A through 2I may be accomplished in 15 seconds for a sample transfer tube 1 length of 6 feet for example.

Figure 2J:
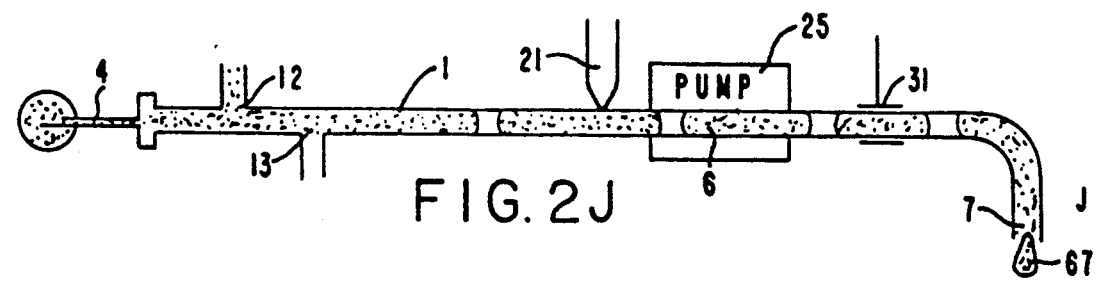

In FIG. 2J all of the blood previously remaining in sample transfer tube 1 as in FIG. 2I has been expelled to the waste site. The entire volume of sample transfer tube is now filled with washing fluid or combinations of washing fluid and bubbles 66 as in FIG. 2G. It will be understood that the number and distance between bubbles in bubble train 66 (FIG. 2G) and the time during which flow of washing fluid and immiscible fluid bubbles in sample transfer tube 1 is sustained may be variable to best accomplish the elimination of blood residues within the sample transfer tube 1.

Figure 2K:
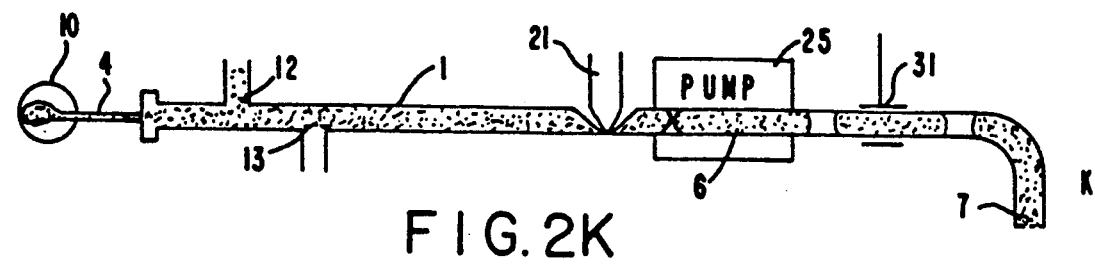

In FIG. 2K pinch valve 21, as operated by logic control, has blocked the sample transfer tube 1 inlet to peristaltic pump 25 such that continued inflow of washing fluid through washing fluid inlet port 12 causes all of the washing fluid flow to be directed through catheter 4 into vessel 10. At this point, the impelling action of peristaltic pump 25 on the washing fluid delivery tube 2 may be reduced to maintain a normal keep open washing fluid flow rate in catheter 4 as 5 milliliters per hour for example. This is easily implemented by logic control 40.

It will be understood that the process steps depicted in FIGS. 2A through 2K are intended to achieve the functions of drawing a blood sample to be tested, dispensing the sample to a test device at a location remote from the site of sample collection, taking steps to maintain the purity of the blood sample so that it remains essentially unaffected from an analysis perspective by its removal from the source vessel 10 and transfer the sample to blood testing device 50, cleaning the surfaces contacted by the blood sample subsequent to the transfer process, and establishing a keep open flow in the catheter 4, maintaining it clear of material such as clotted blood within the vessel 10 after the sampling process has been completed. It will be further understood that the fixed volume of diaphragm pump 14 in FIG. 1 serves to prevent potentially dangerous injection of air or other immiscible fluid into the blood source vessel 10. Furthermore, it will be understood that air bubbles may in fact pass from washing fluid fluid reservoir 9 through washing fluid delivery tube 2. Thus, the bubble detector 18 in FIG. 1 provides protection from immiscible fluid bubble injection into vessel 10 by signaling the logic control module of the presence of such bubbles prior to such injection.

Referring to FIG. 3, there is shown a practical system for blood sample collection, delivery to a remote site and diagnostic analysis. Simply described, the system is divided into permanent and disposable components. The permanent instrument section comprises visual monitor and data input module 43, blood sample collection and delivery system module 51, and blood testing system module 50. These modules are housed in instrument housing 49 that is designed to be suspended from a conventional IV pole via clamps (not shown) or to sit on a convenient horizontal surface. The disposable components include the fluid manifold and bubble detector assembly module 11, tubing and electrical umbilical bundle 8, cassette 34, and washing fluid washing fluid reservoir 9. Not shown are the blood testing device cassettes that reside behind instrument access door 52, and the waste fluid container that resides behind access door 53.

For operator convenience the blood sample disposable is provided as a single assembly that includes catheter 4 connected directly to sample transfer tube 1 and fluid manifold and bubble sensor assembly 11 connected by way of tubing and electrical umbilical bundle 8 to cassette 34. In use, cassette 34 is positioned in a recess 30 of the instrument housing 49. The umbilical 8 is then routed to the site of sampling. After insertion of the catheter 4 into the vessel containing blood to be sampled, the fluid manifold and bubble sensor assembly 11 is taped or otherwise attached to structure adjacent to the site of catheter 4 insertion. This site may be the patient's arm, for example, to thereby provide strain relief for the sample transfer tube 1 and catheter 4 as well as the umbilical 8. The fluid reservoir 9, is a conventional IV bottle or bag of normal washing fluid. The reservoir 9 is attached to the cassette 34 by conventional tubing connector 16 and located adjacent to the instrument housing 49 as IV pole-mounted on the same pole to which the instrument housing 49 is attached.

When properly positioned within the recess 30 of the instrument housing 49, the sampler cassette 34 is maintained in direct contact with interface surface 35, thereby establishing positional relationships between sample transfer tube 1 and washing fluid delivery tube 2. The tubes 1 and 2 are routed through the cassette 34 and interface with the fingers of peristaltic pump 25, pinch valves 21 and 22, and bubble detector 31. Electrical contacts with bubble sensor 18 power and signal wires 19 (FIG. 1) are also made between interface surface 35 and cassette 34. Pneumatic connection between air pump control tube 3 and pneumatic pressure pulse pump 24 (FIG. 1) is similarly established through interface surface 35.

As indicated above, the essence of the apparatus and method is that the equipment directs a sample of blood from a patient's vessel as an artery or a vein or from an extra-corporeal tube through which fluid is being passed continuously. The apparatus can be employed in heart surgery with tubing that goes to the oxygenator or in dialysis wherein the fluid is passed out of the body and goes into a processing unit that cleanses the blood. The unique features of the above-noted system as differentiated from prior art systems is the fact that the collection site is a closed site rather than an open cuvette. In order to keep the inlet clean, the system performs a reverse flow back into the patient utilizing a washing solution which is compatible and non-toxic as for example a washing fluid or any non-toxic isotonic fluid.

Figure 4:
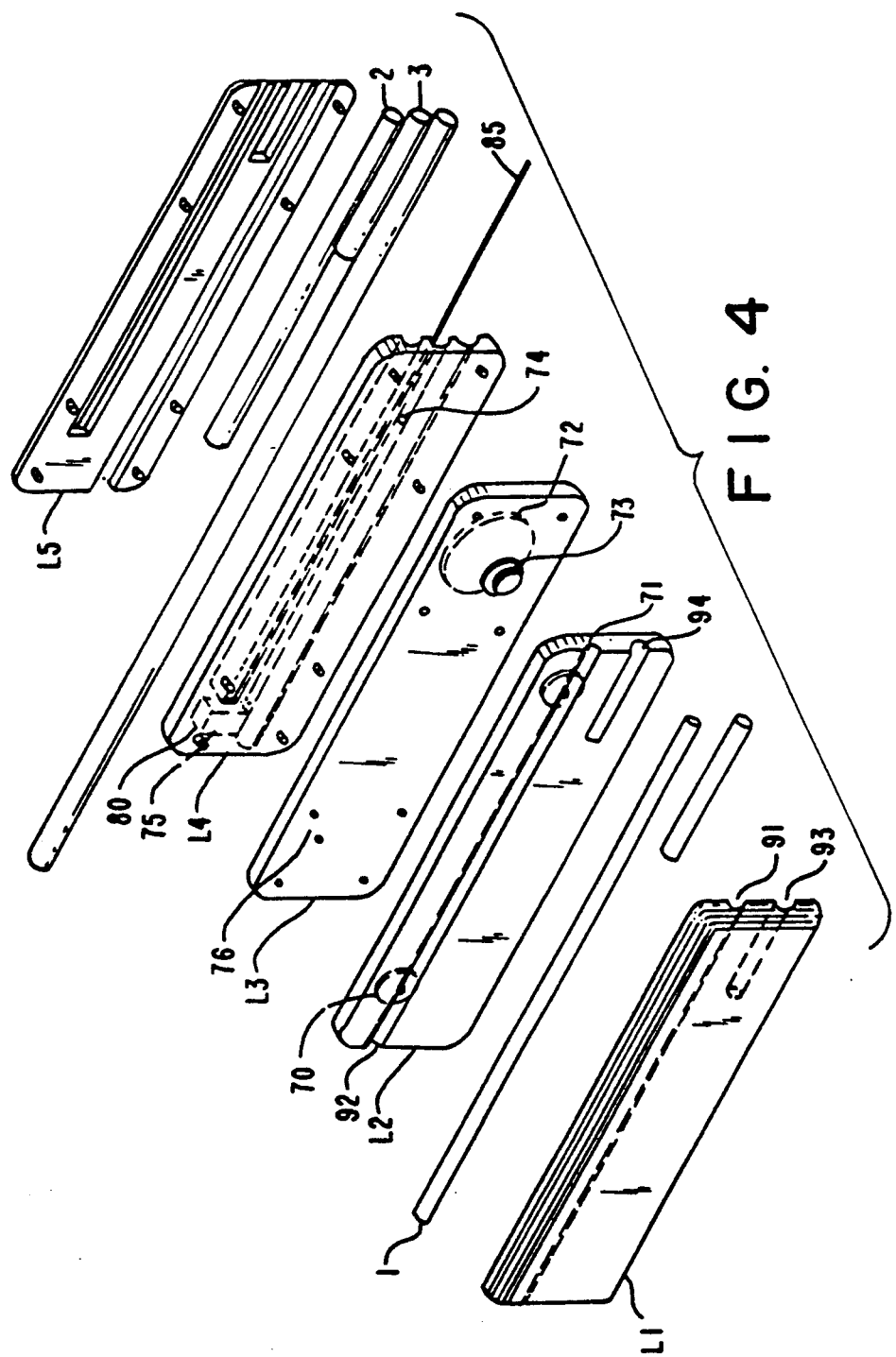
FIG. 4 is a perspective plan view of a fluid manifold and bubble detector assembly comprising a series of interlocked planar members.

Referring to FIG. 4, there is shown a fluid manifold and bubble detector assembly 11 as for example depicted in schematic form in FIG. The module 11 has entering therein the sample tube 1, the pneumatic air pump control tube 3, the washing solution or washing fluid delivery tube 2 as well as the bubble detector power and signal wires 19. These tubes and wires are coupled together to form the umbilical 8 (FIG. 1). As one can ascertain from FIG. 4, the fluid manifold and bubble detector assembly 11 is fabricated from five planar interlocking layers of plastic material designated as L1, L2, L3, L4 and L5. These planar plastic members are preconstructed and preformed and as will be explained sandwich the series of tubes as indicated in FIG. 1 between the various levels. The planar members L1 to L5 also contain a check valve 17 and the diaphragm air pump 14. L1 and L2 as shown sandwich two pieces of tubing therebetween. One tube is the sample line 1 and the other is designated as the bubble air in line. This line is just an air intake which supplies the air that goes into the sample line and under control of the diaphragm pump 14. The tubes are positioned between L1 and L2 by means of congruent grooves or channels as 91, 92, 93 and 94.

The module L2 contains two check valves as well as two small ports which interface with the valves as will be explained. Essentially, the check valves 70 and 71 are disk like valves and operate to perform the function of assuring one way flow of washing fluid into the sample line and diaphragm pump output of immiscible fluid into the sample line. Check valves 70 and 71 are made from silicon rubber, are molded and have a built-in compression seal so that upon assembly the check valve also performs a through-face seal for fluid and air.

These check valves 70 and 71 enable uni-directional flow of air and washing fluid into the sample line 1 and do not permit any backflow of fluid into the air pump or backflow of fluid into the washing fluid source line. The washing fluid check valve 71 is shown in FIG. 1 as valve 17. The module 11 contains a diaphragm air pump 72 which is located in planar member L3. The diaphragm air pump is close coupled on its output side to the sample line. The diaphragm air pump basically has a flapper valve in 73 and a flapper valve out 71. The volume through which the diaphragm travels limits the size of the bubble injected into the sample line 1 regardless of how much pneumatic driving air pressure is applied to the diaphragm.

The diaphragm is a small disk forming a very tiny pump. The air bubble which is injected into the sample line for example is less than 50 millionths of a liter. The small diaphragm with an appropriate seal fits into a well or depression in planar member L3.

As indicated above, the valves 70, 71 and 73 and the diaphragm pump 72 each include an annular elastomeric disk or membrane with a circumferential flange. The flange acts as a seal. The drive air comes in through a port 74 (L4) that sits over the diaphragm of the pump. The port 74 is directed into the drive air in tube 3, which is sandwiched between L4 and L5. The actual pumping action is performed by initially drawing a small vacuum which draws the diaphragm up and then it is driven back down with very little air pressure. Essentially, the diaphragm operates to provide a fixed volume air bubble as long as the diaphragm operates through its full stroke. Thus there is a consistent air bubble size regardless of the amount of air pressure that drives the diaphragm. As one can ascertain, the washing fluid line 2 is directed through and sandwiched between planar members L4 and L5 and is ported straight down to the layers L3 and L2 through the check valve 70 and appropriate apertures. As indicated, the purpose of the check valve 70 is to prevent back flow into the washing fluid line. The washing fluid line 2 is ported to the sample line via apertures located in planar modules L4, L3 and L2 as for example aperture 75 as shown in L4, corresponding aperture 76 in L3 and via the valve 70 through an aperture in L2 at which point the sample line is punctured by means of a pin or other device to provide a washing fluid port. The port allows coupling of the washing fluid line to the sample line through an aperture in the washing fluid line and an aperture in the sample line which apertures communicate with the corresponding apertures in the planar modules (L1-L5).

As seen in FIG. 1, the diaphragm air pump 14 which is the diaphragm pump 72 of FIG. 4 is driven directly by the pneumatic pressure pump 24 which is controlled by the logic control 40 of FIG. 1. In any event, the port for the pneumatic air pump control tube is also sandwiched between modules L5 and L4 and is indicated as the Drive Air In line 3 which functions as line 3 of FIG. 1. The air which is directed through the tube 3 also couples to the diaphragm 76 via apertures in module L4. One, of course, understands that the diaphragm pump 72 is completely analogous to the diaphragm air pump 14 of FIG. 1.

Thus as indicated, the diaphragm pump controls the size of the air bubble which is directed into the sample line. A typical bubble size is about ¼ of an inch or about 7 microliters but can be as much as 50 microliters as controlled by the volume of the diaphragm pump 14. The diaphragm in its relaxed state also serves as a check valve by covering the port to the air out valve 71 thus inhibiting the suctioning of air into the sample line during sampling.

Again, referring to FIG. 4, it is understood that there are three fluid lines that are sandwiched between the planar modules L4 and L5. There is the washing fluid IN line 2, the drive air IN line 3 and a line designated as IV through. This line is just a pass through port in module 11 that allows the user to run a tube back to a pump assembly. This is done if a hospital for example desires to run an intravenous (IV) line without having a separate line. In any event, an IV through line could be accommodated within the fluid manifold and bubble detector assembly 11 and could, in fact, be operated by the peristaltic pump or by a separate pump. As one can ascertain from FIG. 4, within planar member L4 is a module designated by reference numeral 80 and this is the bubble detector as 18 of FIG. 1. The bubble detector wires emanating from module L4 are designated by reference numeral 85. Essentially, bubble detectors are well known and typically they may include an LED and photocell or other devices as well.

A bubble detector as 80 may operate on the principal that air is clear and hence when an air bubble passes by the detector 80, a maximum amount of light would be transmitted. Blood is darker than air and a minimum amount of light would be transmitted when blood is present. Such bubble detectors as indicated are very well known in the art and there are very many different types of devices which can be employed. Bubble detector 80 is associated with a differentiator circuit whereby electronically one monitors the rate which a change occurs between one bubble type and another. The rate of change gives a pulse at the start of a bubble to detect air, blood or washing fluid.

Figure 5:
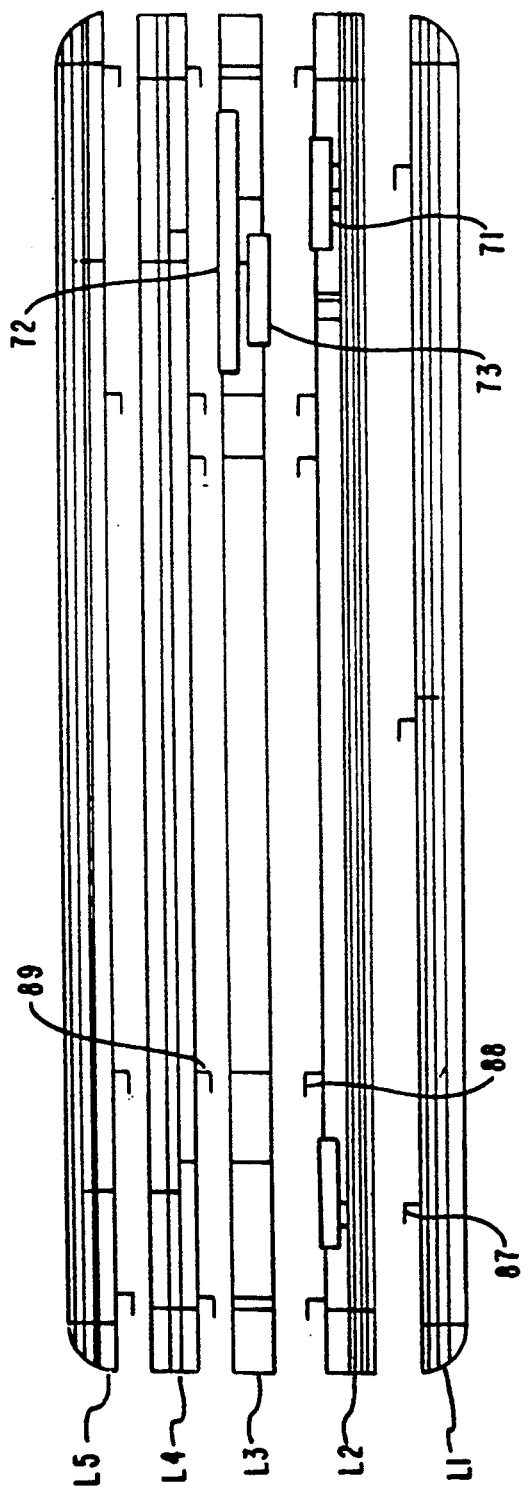
FIG. 5 is a side plan view of the fluid manifold of FIG. 4.

Referring to FIG. 5, there is shown a side view of the various planar modules L1 to L5 shown in FIG. 4. The posts which are shown in FIG. 5 as for example 87, 88, and 89 are actual pins to enable each of the planar modules L1 to L5 to be coupled one to another via the pins 87, 88 and via corresponding apertures. Hence each of the modules L1 to L5 are accurately aligned by means of pins and apertures to interlock to provide the module assembly 11. The various tubes are accommodated or sandwiched between the planar member via channels in the members which accommodate the tubes.

The various layers L1-L5 are connected together by means of ports or apertures in each of the layers to enable one to couple the sample line 1 to the washing fluid line as well as to the source of air, as indicated.

Figure 6:
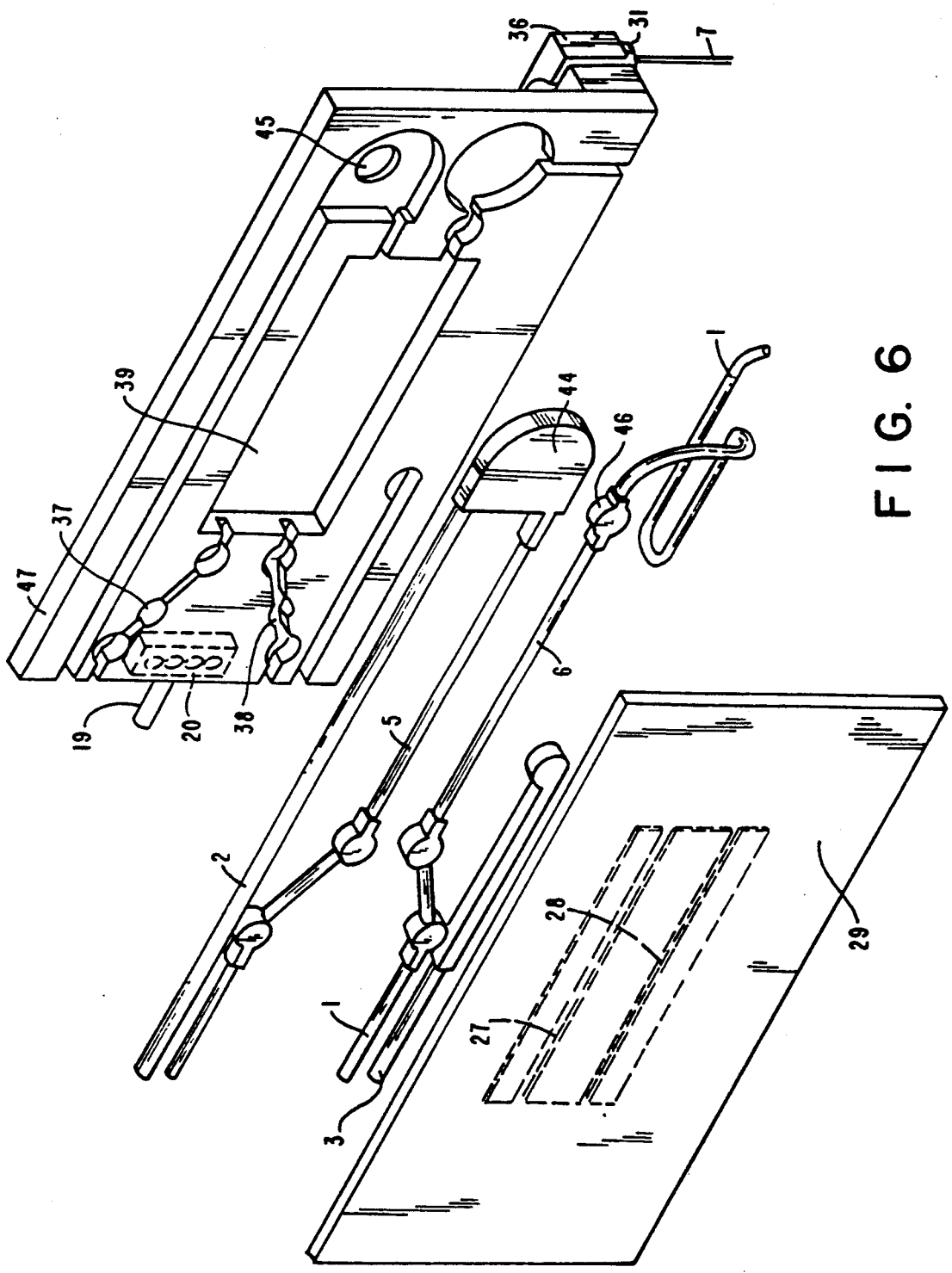
FIG. 6 is a schematic perspective plan view of a pump cassette assembly employed with the therapy control system according to this invention.

Referring to FIG. 6, there is shown the blood sample collection system disposable cassette 34 as shown in FIG. 3. The sample transfer tube 1 is directed through the cassette as is the pneumatic air pump control tube 3 and the washing solution or washing fluid delivery tube 2. The cassette has a front plate 29 which essentially includes a series of indentations. The indentations form a washing fluid delivery tube guide or groove 27 and a sample transfer tube guide or groove 28. These guides 27 and 28 accommodate the washing fluid line 2 and the sample line 1. The grooves 27 and 28 have flat bottom surfaces in order to allow the fingers of the peristaltic pump to coact with the tubes to control fluid flow. As can be seen, the cassette consists of a planar member 29 which is the cassette back cover and a front planar member 47 which is the cassette front cover. Member 47 has a plurality of channels to accommodate the various tubes as shown. It is also shown that the tubes for example are conveniently coupled together by means of suitable devices. The pump cassette assembly 34 also contains an occlusion detector pressure sensor interface port 45. There is shown a sample delivery nozzle pivot arm 36 to enable the cassette to be emplaced and removed from in the housing 40 as shown for example in FIG. 3.

Sample delivery nozzle pivot arm 36 locates a section of the sample tube 1 with respect to a bubble detector 31 shown in FIG. 1 which is located within the blood sample collection and delivery system module 51 shown in FIG. 3. This bubble detector 31 is used to detect and sense the position of the fluids in the output end of sample tube 1.

The front cover of the cassette assembly 47 has an aperture 39 through which the fingers of the peristaltic pump are directed and which engage the sample line and the washing fluid line at areas 5 and 6 to pump fluid in the lines as explained in regard to FIGS. 2A to 2K.

Thus, as one can understand from the above, the system utilizes two disposable modules. One module referred to as the fluid manifold detector assembly 11 is completely disposable and can be placed as indicated on the arm of the patient. The module 11 is small and has the umbilical cord 8 directed therefrom. The cord 8 is also disposable. After the patient has been monitored accordingly, the entire module 11 and cord 8 is thrown away. The second disposable module as shown in FIG. 6 is the therapy control or pump cassette assembly 34. This also contains tubings and the various other parts which can be disposed of. It is, of course, understood that the module 34 need not be disposable but can be fabricated in two parts as a cassette assembly and rearranged for each patient for example by placing new tubing within the cassette assembly.

The sample line is stretched at area 6 with respect to the washing fluid line to change the ratio of the flow rates under the influence of identical peristaltic impeller action. The stretch typically changes the flow between 0 and 25 percent.

Thus, as indicated, there is described a system which is a blood sampling apparatus system which allows one to take a sample of blood from a vessel of a patient or extracorporeal port and which sample is passed continuously to a test location. The entire system relies on the fact that the inlet or the collection site is a closed site. The inlet site can be cleaned by a back flushing operation whereby fluid flow is reversed and the entire monitoring procedure can operate continuously utilizing the same blood vessel. The system eliminates the need for constant blood samples to be taken from a patient through finger pricks or other standard devices, while allowing continuous monitoring and testing as desired.

We claim:

1. Apparatus for transporting a sample of body fluid such as blood from a first location to a test site location, comprising:

sample tubing means having at a first end a first sample input port, a second washing fluid input port and a third input port for receiving a fluid which is relatively immiscible with said sample and said washing fluid and having at a second end an output port, washing fluid tubing means coupled to said second washing fluid input port, a first pumping means coupled to said sample tubing means operative to direct the flow of fluids to said output port, second pumping means coupled to said washing fluid tubing means operative to direct the flow of washing fluid through said second washing fluid input port into said sample tubing means and co-operative with said first pumping means to control the ratio of fluid volumes pumped by said first pumping means and said second pumping means in a first mode of operation to thereby cause washing fluid to flow within said sample tubing means from said washing fluid input port towards both said sample input port and said output port, first valving means coupled to said sample tubing means operative when selected in a second mode of operation to impede the flow of fluids to said output port thereby to divert all the flow of washing fluid from said washing fluid input port to said sample input port, second valving means coupled to said second washing fluid tubing means operative when selected in a third mode of operation to impede the flow of washing fluid through said second washing fluid input port into said sample tubing means, third metered pumping means coupled to said third input port for injecting a controlled volume of said immiscible fluid through said third input port when selected in said first and third modes of operation to thereby produce in said sample tubing means a series of discrete immiscible fluid bubbles dispersed within said body fluid or said washing fluid, control means coupled to said pumping means and said valving means for selectively energizing said pumping and said valving means in predetermined sequences to cause said output port to receive a given sequence of fluids as a series of cells of washing fluid separated by bubbles of said immiscible fluid in said first mode of operation or as a series of cells of body fluid separated by bubbles of said immiscible fluid following said third mode of operation, said output port directed to a remote location including said test site, detecting means coupled to said sample tubing means at said remote location for monitoring said sequence of fluids and for providing output signal levels indicative of samples, washing fluid and immiscible fluid at said remote location and, means coupled to said sample tubing means and responsive to said output signal levels for moving said second end of said sample tubing to said test site location when said output signal is indicative of the presence of sample as contained in said series of cells of body fluids whereby only the contents of one selected cell of body fluid is directed to said test site location when said second end is moved and for discarding said body fluid, washing fluid and immiscible fluid in response to said signal levels when the selected cell of body fluid is not detected.

2. The apparatus according to claim 1 wherein said immiscible fluid is air and sample of body fluid is blood.

3. The apparatus according to claim 1 wherein said first and second pumping means includes a peristaltic pump means having a series of fingers operative to pump fluid within a tube towards a remote location with a first channel adapted to receive said sample tubing means and a second channel adapted to receive said washing fluid tubing means with said channels positioned with respect to said fingers to cause said pump to pump both sample and washing fluid via said tubing means.

4. The apparatus according to claim 2, wherein said washing solution is injectable normal saline.

5. The apparatus according to claim 3 wherein the diameter of said sample tubing means is different from the diameter of said washing fluid tubing means to thereby obtain a different flow rate of sample with respect to washing fluid.

6. The apparatus according to claim 1 wherein said first sample input port is coupled to a catheter for insertion into a blood accommodating vessel associated with a patient.

7. The apparatus according to claim 1 wherein said sample tubing means and said washing fluid tubing means include flexible plastic tubes for accommodating said fluids.

8. The apparatus according to claim 1 wherein said washing fluid input port is coupled to a washing fluid reservoir via a flexible plastic tube.

9. The apparatus according to claim 5 wherein said first valving means is a pinch valve operative when selected to pinch said sample tubing means to block the flow of fluid to said output port.

10. The apparatus according to claim 1 wherein said second valving means is a pinch valve operative when selected to block the flow of washing fluid from said reservoir.

11. The apparatus according to claim 2 wherein said third metered pumping means is a diaphragm pump coupled to a pressure pump for operating said diaphragm to provide a controlled volume of immiscible fluid to be directed through said third input port to said sample tubing means.

12. The apparatus according to claim 1 wherein said detecting means is a bubble detector operative to detect the transitions between said cells of sample, washing fluid and immiscible fluid.

13. The apparatus according to claim 1 including a fluid dispensing nozzle coupled to said output port of said sample tubing means.

14. The apparatus according to claim 3 further including a bubble detector coupled to said sample tubing means near said catheter to detect any bubbles.

15. Apparatus for transporting a sample of body fluid such as blood from a first location to a test site location, comprising:

a fluid manifold means having a first sample input port, a second washing fluid input port and a third input port for receiving a medium which is relatively immiscible with said sample and said washing fluid, and having sample tubing means coupling said first, second and third input ports, said fluid manifold means having selectively operable first pump means located thereon, with said first pump means coupled to said third input port to direct a cell of said immiscible fluid into said sample tubing means when said first pump is operated with said cell operative to separate sample from washing fluid, control means coupled to said first pump means for selectively energizing said pump means in predetermined sequences to cause said sample tubing means to receive a given sequence of matter as a first volume of washing fluid followed by a second volume of said immiscible medium followed by a third volume of body fluid, followed by a fourth volume of immiscible medium followed by a fifth volume of body fluid, followed by a sixth volume of immiscible medium, followed by a seventh volume of washing fluid, said sample tubing means directed from said manifold means at one end to a remote location including said test site at an output end, said sample tubing means having detecting means at said remote location for monitoring said sequence of matter and for providing at an output signal levels indicative of sample, washing fluid and immiscible material at said remote location and, means coupled to said sample tubing means and responsive to said signal levels for moving the output end of said sample tubing to said test site when said detected signal is indicative of the presence of sample as contained in said third volume whereby only sample is directed to said test site when said output end of said sample tubing is moved and for dispensing said washing fluid, immiscible medium in response to said signal levels when sample is not detected.

16. The apparatus according to claim 15, wherein said immiscible medium is air and said body fluid is blood.

17. The apparatus according to claim 15, wherein said washing fluid is injectable normal saline.

18. The apparatus according to claim 15, wherein said first sample input port is coupled to a catheter for insertion into the blood vessel of a patient.

19. The apparatus according to claim 15, wherein said first sample input port is coupled to a source of extracorporeal blood flow.

20. The apparatus according to claim 15, wherein said second washing fluid input port is coupled to one end of a flexible tube with the other end coupled to a washing fluid reservoir.

21. The apparatus according to claim 15, wherein said sample tubing means includes second pumping means for moving said sequence of material from said sample output port.

22. The apparatus according to claim 21, wherein said second pumping means is a peristaltic pump.

23. The apparatus according to claim 15, wherein said sample tubing means has a nozzle located at said output end for dispensing said materials.

24. The apparatus according to claim 15, wherein said tubing means includes a cassette housing for holding a sample tubing means and a washing fluid tube section between input and output ports of said cassette housing and having an aperture across which said sample and washing fluid tube sections are directed to enable said tubes to contact said pumping means when said cassette is placed in a predetermined position with respect to said pumping means.

25. The apparatus according to claim 15, further including detecting means positioned near said first input port and operative to detect bubbles in said fluid manifold means to provide a signal output indicative of a problem condition and means coupled to said control means and responsive to said signal to prevent said energization of said first and second pump means.

26. The apparatus according to claim 15 wherein said fluid manifold means includes valve means coupled to said washing fluid and sample tubes to assure unidirectional flow and including said first pump means for directing a predetermined volume of air into said sample tube.

27. A method of transporting a sample of body fluid from a first location to a remote location including a test site, comprising the step of:

positioning a flexible tube between said first location and said remote location indicative of a body fluid sample carrying line, joining said tube at said first location to a source of body fluid at one point, a source of immiscible fluid at another point and a source of washing fluid at still another point, first directing washing fluid through said tube to cause said washing fluid to travel through said tube to enter said first location and simultaneously directing washing fluid towards said remote location, then removing body fluid from said first location and directing said fluid towards said remote location, then directing a first volume of immiscible fluid into said tube to provide a barrier between said sample and said washing fluid and then directing a second volume of immiscible fluid into said tube to provide another barrier by locating said sample between said barriers and then directing another volume of washing fluid into said tube, detecting said sample as located between said barriers at said remote location and depositing said sample as detected at said test site, then directing washing fluid through said tube to cause the washing fluid to travel simultaneously toward said first location and said remote location from said source of washing fluid and introducing a series of said immiscible bubbles in the fluid as directed toward said remote location to wash said sample tube of body fluid deposits prior to repeating the step of first directing.

28. The method according to claim 27, wherein the step of directing immiscible fluid includes pumping a predetermined volume of fluid into said tube to provide a given volume barrier.

29. The method according to claim 27, wherein the steps of directing includes pumping said fluids through said tube as directed into said tube.

30. The method according to claim 28, wherein pumping is accommodated by peristaltic pumping.

31. The method according to claim 28, further wherein the step of detecting includes detecting all fluids in said tube at said remote location to determine fluids which are not sample fluid, and discharging said fluids from said tube at said remote location or waste fluids.

32. The method according to claim 31, wherein said waste fluids are discharged at a waste site.

33. The method according to claim 31, wherein sample fluid is discharged at a test site.

34. The method according to claim 31, wherein sample fluid is discharged at a sample site.

* * * * *